(12) United States Patent
Chang

(10) Patent No.: US 10,759,817 B2
(45) Date of Patent: Sep. 1, 2020

(54) GADOLINIUM COMPLEX, METHOD FOR SYNTHESIS OF THE GADOLINIUM COMPLEX, AND MRI CONTRAST AGENT INCLUDING THE GADOLINIUM COMPLEX

(71) Applicant: Kyungpook National University Industry-Academic Cooperation Foundation, Daegu (KR)

(72) Inventor: Yong Min Chang, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 0 days.

(21) Appl. No.: 16/362,003

(22) Filed: Mar. 22, 2019

(65) Prior Publication Data

US 2019/0292206 A1 Sep. 26, 2019

(30) Foreign Application Priority Data

Mar. 22, 2018 (KR) ........................ 10-2018-0033391

(51) Int. Cl.
| | |
|---|---|
| *C07F 5/00* | (2006.01) |
| *A61K 49/10* | (2006.01) |
| *A61K 47/08* | (2006.01) |
| *A61K 47/18* | (2017.01) |

(52) U.S. Cl.
CPC ............ *C07F 5/003* (2013.01); *A61K 49/108* (2013.01); *A61K 47/08* (2013.01); *A61K 47/18* (2013.01)

(58) Field of Classification Search
CPC .......... A61K 47/18; A61K 49/108; C07F 5/00
See application file for complete search history.

(56) References Cited

PUBLICATIONS

Manuel Tropiano et al. Kinetically Stable Lanthanide Complexes Displaying Exceptionally High Quantum Yields upon Long-Wavelength Excitation: Synthesis, Photophysical Properties, and Solution Speciation, Inorganic Chemistry, 54, 3337-3345. (Year: 2015).*

* cited by examiner

*Primary Examiner* — Michael G. Hartley
*Assistant Examiner* — Jagadishwar R Samala
(74) *Attorney, Agent, or Firm* — Norton Rose Fulbright US LLP

(57) ABSTRACT

Disclosed are a gadolinium complex with a high relaxibity at a high magnetic field, a method for synthesizing the complex, and an MRI contrast agent containing the gadolinium complex. The gadolinium complex may be expressed as a Chemical Formula 1:

[Chemical Formula 1]

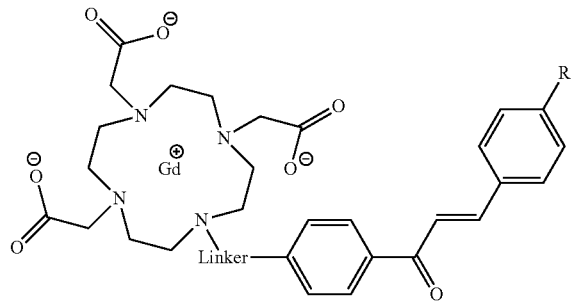

17 Claims, 3 Drawing Sheets

[FIG. 1]
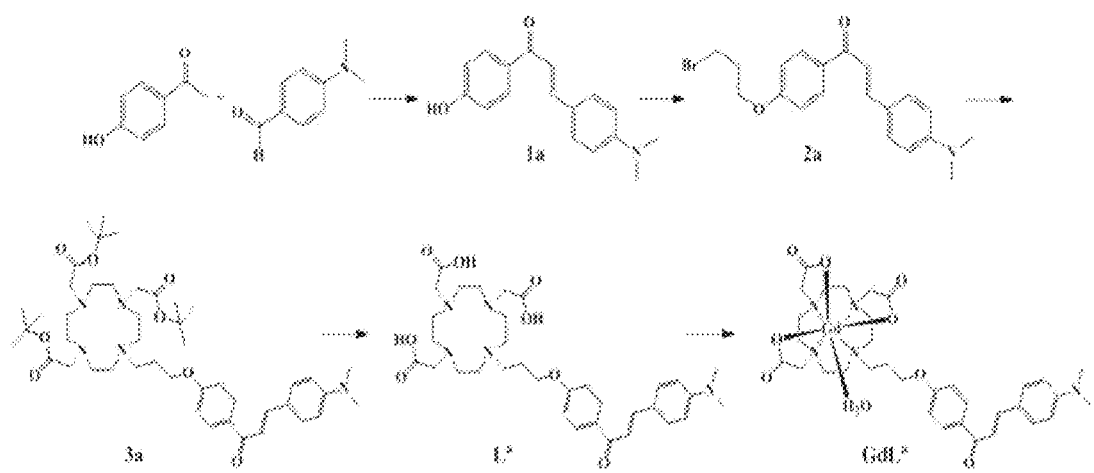
[FIG. 2]
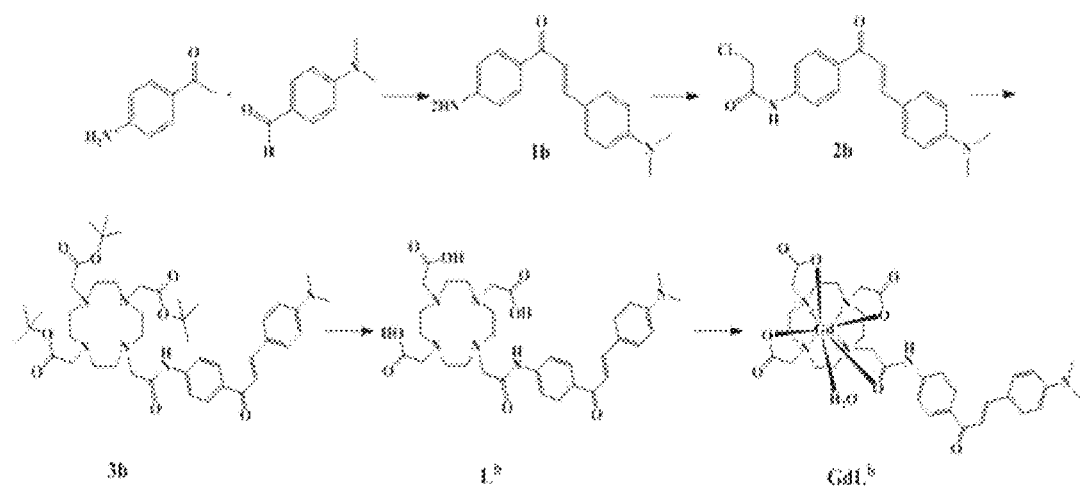

[FIG. 3]
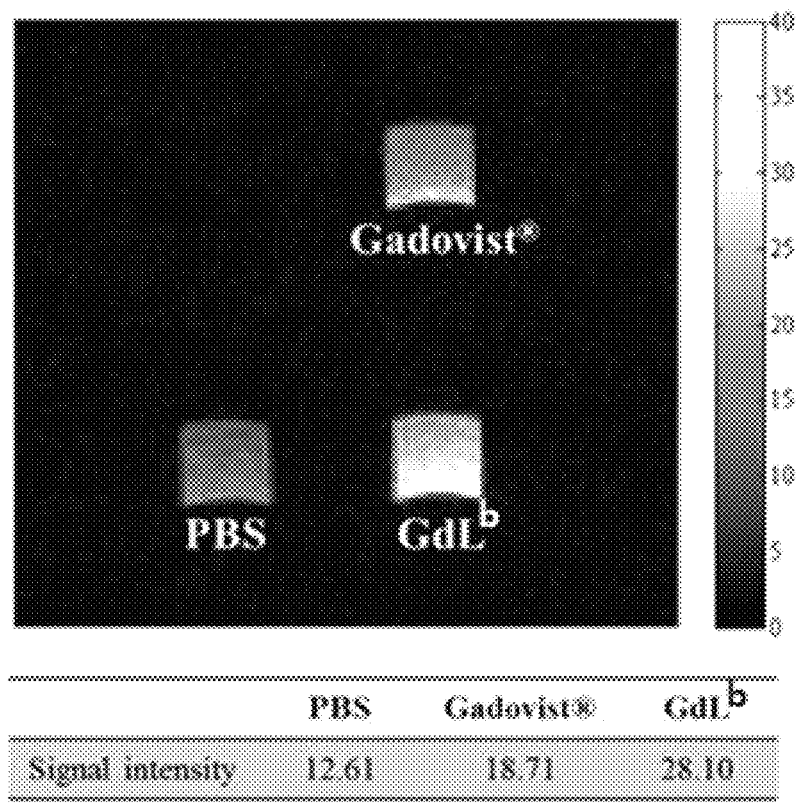

[FIG. 4]
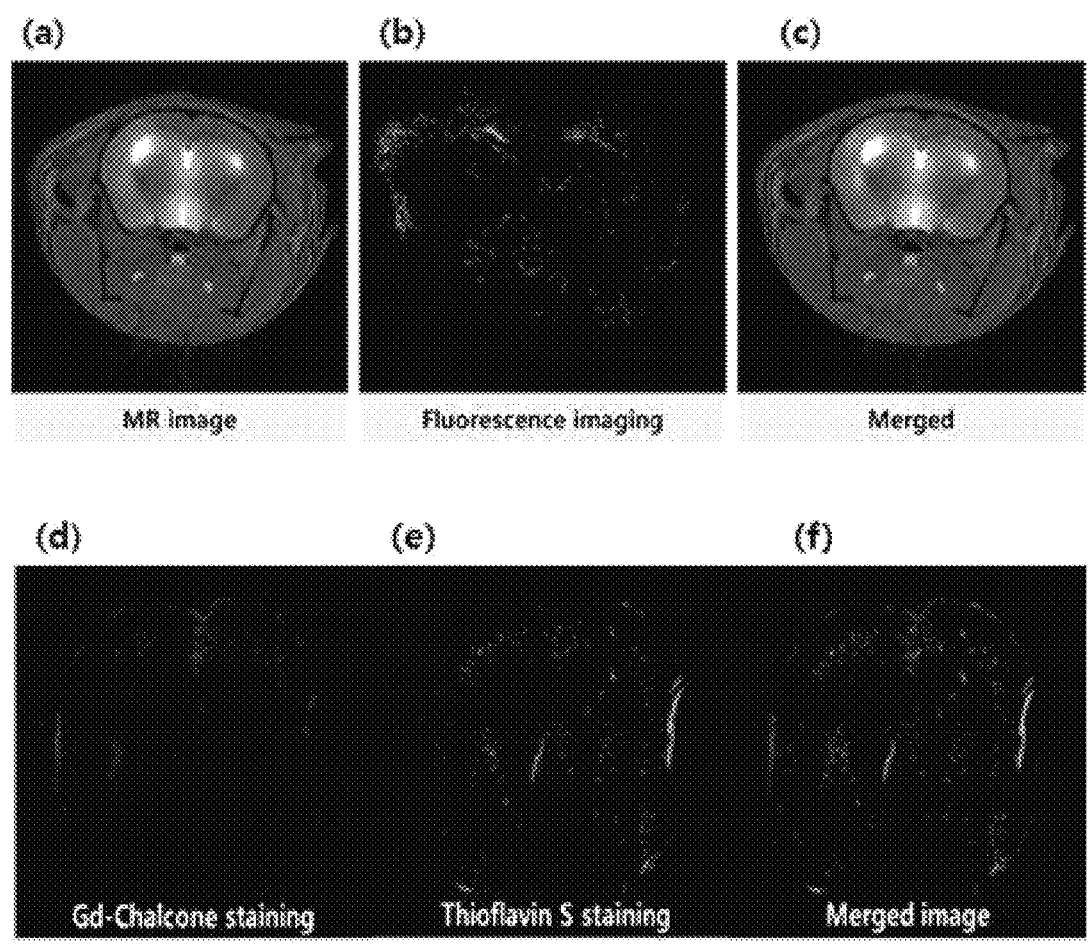

GADOLINIUM COMPLEX, METHOD FOR SYNTHESIS OF THE GADOLINIUM COMPLEX, AND MRI CONTRAST AGENT INCLUDING THE GADOLINIUM COMPLEX

CROSS-REFERENCE TO RELATED APPLICATION

This application claims a benefit under 35 U.S.C. § 119 a of Korean Patent Application No. 10-2018-0033391 filed on Mar. 22, 2018, on the Korean Intellectual Property Office, the entire disclosure of which is incorporated herein by reference for all purposes.

BACKGROUND

1. Field

The present disclosure relates to a gadolinium complex, a method for synthesizing the complex, and an MRI contrast agent including the complex. More particularly, the present disclosure relates to a gadolinium complex as an MRI contrast agent with high relaxibity at a high magnetic field, a method for synthesizing the complex, and an MRI contrast agent.

2. Description of Related Art

Magnetic Resonance Image (MRI) refers to a method of acquiring anatomical, physiological, and biochemical information images of a body using spin relaxation of hydrogen atoms in a magnetic field. The MRI is a non-invasive method and is rendered in a real time.

A contrast between tissues on images obtained via MRI is caused by the fact that a relaxation in which a water molecule nuclear spin in a tissue returns to an equilibrium is different between types of tissues. The contrast agent affects this relaxation to increase a difference in the relaxation between the types of tissues and thus to cause a MRI signal change, thereby making the contrast between the types of the tissues clearer. As the contrast agent, gadolinium-based contrast agents have been widely used since the FDA approved the gadolinium-based contrast agent for MRI based in 1988.

The contrast agent should be thermodynamically stable, be water-soluble, and bind to at least one water molecule to have a high magnetic relaxation with water. However, the gadolinium-based contrast agents that are commercially available have low water solubility and relaxivity. In particular, gadolinium-based contrast agents such as gadobutrol known under the trade names Gadavist® or Gadovist® or gadolinium-based contrast agents known under the trade names Magnevist (trade name) and Dotarem (trade name) have low relaxivity in high magnetic field conditions. Therefore, there is a continuing need for development of optimized MRI contrast agents.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

One purpose of the present disclosure is to provide a gadolinium complex with a novel structure, which is used as an MRI contrast agent, and which has a high relaxivity in a high magnetic field that targets beta amyloid (Aβ).

Another purpose of the present disclosure is to provide a method for preparing the gadolinium complex.

Still another objective of the present disclosure is to provide an MRI contrast agent containing the novel structure of the gadolinium complex.

In a first aspect of the present disclosure, there is provided a gadolinium complex expressed as a following Chemical Formula 1:

[Chemical Formula 1]

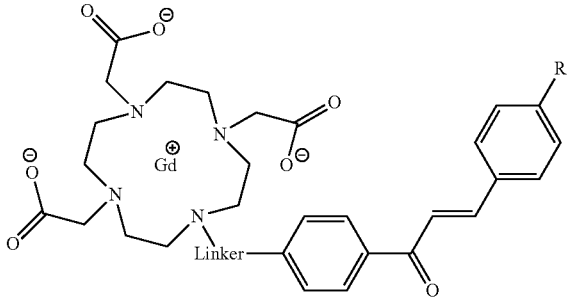

In the Chemical Formula 1, the linker represents *—$(CH_2)_n$-A-*, n indicates an integer of 0 to 5, A represents *—COO—*, *—CO—*, *—CONH—*, *—O—* or *—$C_5N(R_aR_b)$—*, R represents a hydrogen atom, a hydroxyl group, an alkyl group having 1 to 5 carbon atoms, an alkoxy group having 1 to 5 carbon atoms, an aryl group having 5 to 20 carbon atoms, a heteroaryl group having 4 to 20 carbon atoms or *—$NR_1R_2$, each of $R_a$, $R_b$, $R_1$ and $R_2$ independently represents a hydrogen atom or an alkyl group having 1 to 5 carbon atoms.

In this connection, "*—$C_5N(R_aR_b)$—*" which may be A in the Chemical Formula 1 means pyridinylene having $R_a$ and $R_b$ as functional groups.

In one embodiment of the first aspect, gadolinium in the gadolinium complex may be coordinated with at least one water molecule.

In one embodiment of the first aspect, the gadolinium complex exhibits a relaxivity of greater than or equal to 4 $mM^{-1}s^{-1}$.

In one embodiment of the first aspect, the gadolinium complex has a relaxibity ($r_1$) dependent on a $T_1$ relaxation time obtained based on an inversion time and a relaxibity ($r_2$) dependent on a $T_2$ relaxation time obtained based on an echo time, wherein each of the relaxibity ($r_1$) and relaxibity ($r_2$) is greater than or equal to 4 $mM^{-1}s^{-1}$ in a high magnetic field range of 7 T or greater.

In one embodiment of the first aspect, the gadolinium complex exhibits a relaxivity of 4 $mM^{-1}s^{-1}$ to 7 $mM^{-1}s^{-1}$ in a high magnetic field range of 7 T to 10 T.

In a second aspect of the present disclosure, there is provided a MRI contrast agent containing the gadolinium complex expressed as the Chemical Formula 1.

In one embodiment of the second aspect, gadolinium in the gadolinium complex may be coordinated with at least one water molecule.

In one embodiment of the second aspect, the MRI contrast agent exhibits a relaxivity of greater than or equal to 4 $mM^{-1}s^{-1}$.

In one embodiment of the second aspect, the gadolinium complex has a relaxibity ($r_1$) dependent on a $T_1$ relaxation time obtained based on an inversion time and a relaxibity ($r_2$) dependent on a $T_2$ relaxation time obtained based on an echo time, wherein each of the relaxibity ($r_1$) and relaxibity ($r_2$) is greater than or equal to 4 $mM^{-1}s^{-1}$ in a high magnetic field range of 7 T or greater.

In one embodiment of the second aspect, the MRI contrast agent exhibits a relaxivity of 4 $mM^{-1}s^{-1}$ to 7 $mM^{-1}s^{-1}$ in a high magnetic field range of 7 T to 10 T.

In one embodiment of the second aspect, the gadolinium complex represented by the Chemical Formula 1 may include at least one water molecule coordinated with gadolinium.

In one embodiment of the second aspect, the MRI contrast agent is a beta amyloid-targeting MRI contrast agent that targets a beta amyloid oligomer. In this connection, the contrast agent may target an oligomeric beta amyloid.

In a third aspect of the present disclosure, there is provided a method for producing a gadolinium complex, the method including:

synthesizing a chalcone-based compound represented by a following Chemical Formula 1-1;

[Chemical Formula 1-1]

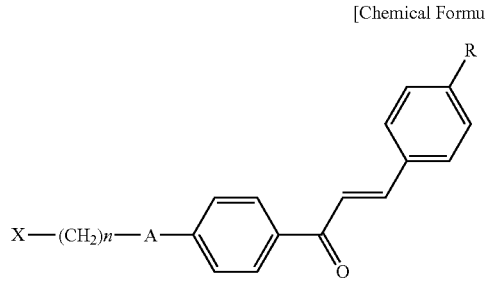

synthesizing a compound represented by a following Chemical Formula 1-2 using the compound represented by the Chemical Formula 1-1;

[Chemical Formula 1-2]

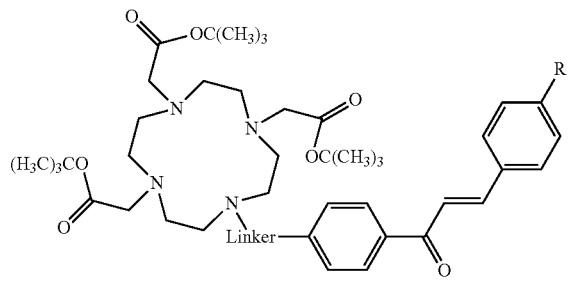

producing a ligand represented by a following Chemical Formula 1-3 using the compound represented by the Chemical Formula 1-2;

[Chemical Formula 1-3]

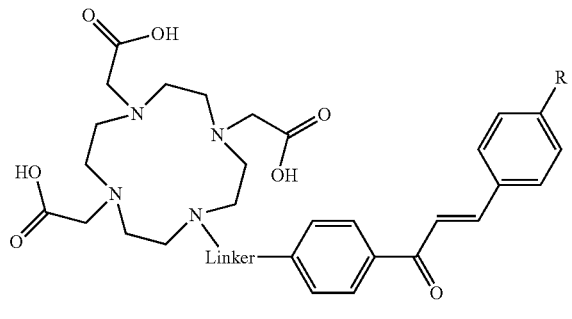

synthesizing a gadolinium complex represented by a following Chemical Formula 1 using the compound represented by the Chemical Formula 1-3 and gadolinium chloride hexahydrate:

[Chemical Formula 1]

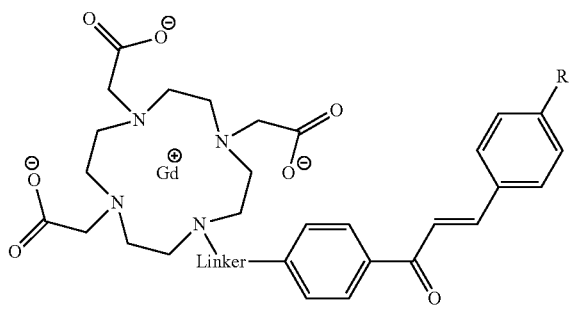

where in the Chemical Formula 1-1, X represents a halogen atom, where the linker in each of the Chemical Formulas 1-2 and 1-3 and Chemical Formula 1 represents *—$(CH_2)_n$-A-*, where in the Chemical Formula 1-1 and in the linker of each of the Chemical Formulas 1-2, and 1-3 and Chemical Formula 1, n represents an integer of 0 to 5, where A represents *—COO—*, *—CO—*, *—CONH—*, *—O—* or *—$C_5N(R_aR_b)$—*, where R represents a hydrogen atom, a hydroxyl group, an alkyl group having 1 to 5 carbon atoms, an alkoxy group having 1 to 5 carbon atoms, an aryl group having 5 to 20 carbon atoms, a heteroaryl group having 4 to 20 carbon atoms or *—$NR_1R_2$, where each of $R_a$, $R_b$, $R_1$ and $R_2$ independently represents a hydrogen atom or an alkyl group having 1 to 5 carbon atoms.

In one embodiment of the third aspect, synthesizing the chalcone-based compound comprises mixing and reacting p-hydroxyacetophenone, a KOH aqueous solution and p-dimethylaminobenzaldehyde with methanol to obtain a precipitate; and reacting the precipitate with 1,3-dibromopropane to produce a compound having the Chemical Formula 1-1 in which R is a dimethylamine group, n is 3, A is *—O—*, and X is Br.

In one embodiment of the third aspect, synthesizing the chalcone-based compound comprises mixing and reacting 4'-aminoacetophenone, KOH aqueous solution, p-dimethylaminobenzaldehyde with ethanol to obtain a precipitate; and reacting the precipitate with chloroacetyl chloride to produce a compound having the Chemical Formula 1-1 in which R is a dimethylamine group, n is 1, A is *—CONH—*, and X is Cl.

In accordance with the novel structure of the gadolinium complex, the method for synthesizing the complex and the MRI contrast agent according to the present disclosure, the gadolinium complex has the high relaxibity in the high magnetic field and satisfies the properties required as the contrast agent. Thus, the contrast-enhancing effect may be improved using a low content of the gadolinium complex even in a high magnetic field. Further, the structure of the gadolinium complex according to the present disclosure is based on the structure in which gadolinium is coordinated with water molecules so that gadolinium ions may not be easily dissociated. Thus, biostability of the contrast agent is high.

The gadolinium complex according to the present disclosure may target the beta amyloid oligomers and thus may be widely used as an MRI contrast agent targeting the beta amyloid oligomers.

BRIEF DESCRIPTION OF THE DRAWINGS

FIG. 1 is a diagram for illustrating a method for synthesizing a gadolinium complex (GdL$^a$) according to an embodiment of the present disclosure.

FIG. 2 is a diagram for illustrating a method for synthesizing a gadolinium complex (GdL$^b$) according to one embodiment of the present disclosure.

FIG. 3 shows in vitro binding affinity of the gadolinium complex (GdL$^b$) to a beta amyloid oligomer according to one embodiment of the present disclosure.

FIG. 4 shows comparison between in vivo MR imaging analysis using the gadolinium complex (GdL$^b$) and ex vivo fluorescence image for a dementia disease model according to one embodiment of the present disclosure.

DETAILED DESCRIPTIONS

In a following detailed description of the present disclosure, numerous specific details are set forth in order to provide a thorough understanding of the present disclosure. However, it will be understood that the present disclosure may be practiced without these specific details. In other instances, well-known methods, procedures, components, and steps have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present disclosure provides a gadolinium complex expressed as a following Chemical Formula 1:

[Chemical Formula 1]

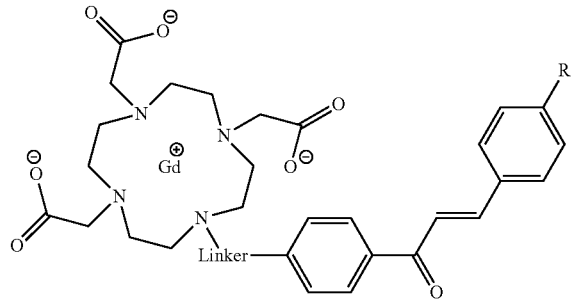

in the Chemical Formula 1, the liner represents *—(CH$_2$)$_n$-A*, n indicates an integer of 0 to 5, A represents *—COO—*, *—CO—*, *—CONH—*, *—O—* or *—C$_5$N(R$_a$R$_b$)—*, R represents a hydrogen atom, a hydroxyl group, an alkyl group having 1 to 5 carbon atoms, an alkoxy group having 1 to 5 carbon atoms, an aryl group having 5 to 20 carbon atoms, a heteroaryl group having 4 to 20 carbon atoms or *—NR$_1$R$_2$, each of R$_a$, R$_b$, R$_1$ and R$_2$ independently represents a hydrogen atom or an alkyl group having 1 to 5 carbon atoms.

In this connection, "*—C$_5$N(R$_a$R$_b$)—*" which may be A in the Chemical Formula 1 means pyridinylene having R$_a$ and R$_b$ as functional groups.

In one embodiment, gadolinium in the gadolinium complex may be coordinated with at least one water molecule. That is, in the gadolinium complex represented by the Chemical Formula 1, gadolinium may be coordinated with at least one water molecule. For example, in the gadolinium complex represented by the Chemical Formula 1, gadolinium may be coordinated with one or two water molecules.

When, in the gadolinium complex represented by the Chemical Formula 1, A is COO, CO or CONH, the oxygen atom of A may form a coordination bond with gadolinium.

The gadolinium complex represented by the Chemical Formula 1 in accordance with the present disclosure exhibits a high relaxibity in high magnetic fields. In this connection, the high magnetic field means at least 7 T (tesla).

In one embodiment, the high magnetic field range in which the gadolinium complex expressed by the Chemical Formula 1 exhibits the high relaxibity may be in a range of 7 T to 10 T.

The relaxibity (unit: mM$^{-1}$s$^{-1}$) means a self-relaxation rate (an inverse of a relaxation time (s)) which the contrast agent at a concentration (gadolinium concentration) 1 mM exhibits. This relaxibity may refer to a numerical value of a contrast-enhancing effect by the 1 mM contrast agent. The contrast agent with the high relaxibity exhibits a high contrast-enhancing effect even at a relatively small dose. However, the relaxibity is exhibited to be lower in the high magnetic field range as the magnetic field strength increases. That is, the contrast-enhancing effect of the contrast agent is lowered in the high magnetic field. Thus, to compensate for this deterioration, the amount of the contrast agent as dosed should be increased.

However, the gadolinium complex represented by the Chemical Formula 1 in accordance with the present disclosure exhibits a relaxivity of at least 4 mM$^{-1}$s$^{-1}$ in a high magnetic field. Thus, the contrast-enhancing effect may be improved using a low content of the present gadolinium complex even at the high magnetic fields.

In accordance with the present disclosure, the relaxibity (unit mM$^{-1}$ s$^{-1}$) is obtained using an inversion recovery according to the inversion time (T1). More specifically, signal intensities at varying inversion times T1 are acquired. Then, the signal intensities are subjected to a minimum non-linear fitting (NLF) to obtain the relaxation time (s). Then, the relaxibity (unit mM$^{-1}$ s$^{-1}$) is obtained using the relaxation time (s) and the concentration (mM) of the contrast agent. The gadolinium complex represented by the Chemical Formula 1 has the relaxibity defined as above which is at least 4 mM$^{-1}$ s$^{-1}$ not only in the normal magnetic field range of 1.5 T but also in the high magnetic field of 7 T or greater.

In accordance with the present disclosure, an example of the gadolinium complex represented by the Chemical Formula 1 may be a compound represented by a following Chemical Formula 2:

[Chemical Formula 2]

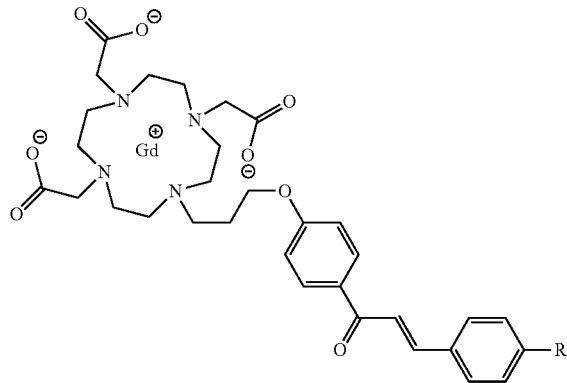

In the Chemical Formula 2, R represents a hydrogen atom, a hydroxyl group, an alkyl group having 1 to 5 carbon atoms, an alkoxy group having 1 to 5 carbon atoms, an aryl group having 5 to 20 carbon atoms, a heteroaryl group having 4 to 20 carbon atoms or *—NR$_1$R$_2$. R$_1$ and R$_2$ each independently represent a hydrogen atom or an alkyl group having 1 to 5 carbon atoms.

In one example, in the gadolinium complex expressed by the Chemical Formula 2, gadolinium may be coordinated with one water molecule.

For example, in the Chemical Formula 2, R may be a dimethylamine group represented by *—N(CH$_3$)$_2$.

In accordance with the present disclosure, another example of the gadolinium complex represented by the Chemical Formula 1 may be a compound represented by a following Chemical Formula 3:

[Chemical Formula 3]

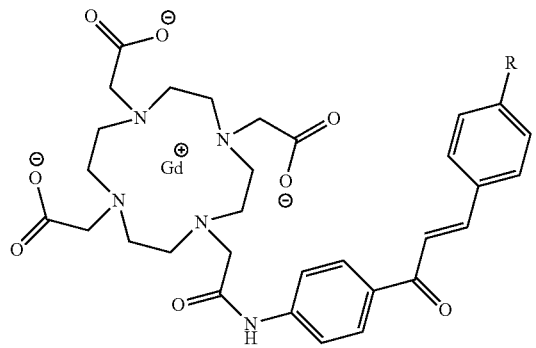

In the Chemical Formula 3, R represents a hydrogen atom, a hydroxyl group, an alkyl group having 1 to 5 carbon atoms, an alkoxy group having 1 to 5 carbon atoms, an aryl group having 5 to 20 carbon atoms, a heteroaryl group having 4 to 20 carbon atoms or *—NR$_1$R$_2$. R$_1$ and R$_2$ each independently represent a hydrogen atom or an alkyl group having 1 to 5 carbon atoms.

In one example, in the gadolinium complex expressed by the Chemical Formula 3, gadolinium may be coordinated with one water molecule. In this connection, the gadolinium may further be coordinated with an oxygen atom in CONH.

For example, in the Chemical Formula 3, R may be a dimethylamine group represented by *—N(CH$_3$)$_2$.

The gadolinium complex according to the present disclosure as described above may be used as a beta amyloid-targeting contrast agent to target the beta amyloid.

Further, according to the present disclosure, the gadolinium complex may be used as an MRI contrast agent and have an effect of enhancing a brightness of an image signal.

Hereinafter, synthesis examples of the gadolinium complexes and characteristics of the synthesized gadolinium complexes according to specific embodiments of the present disclosure will be described.

Synthesis of Gadolinium Complex (GdL$^a$)

FIG. 1 is a diagram for illustrating a method for synthesizing a gadolinium complex (GdL$^a$) according to an embodiment of the present disclosure. The gadolinium complex (GdL$^a$) according to one embodiment of the present disclosure was synthesized using a synthesis procedure as shown in FIG. 1. A compound $^1$H NMR as synthesized in the production process was identified via measurement using a Bruker Advance 400 or 500 spectrometer (Korea Basic Science Research Institute).

(1) Synthesis of Compound 1a

P-hydroxyacetophenone (1 eq.), 40 mL of a 50% KOH aqueous solution and p-dimethylaminobenzaldehyde (1.06 eq.) were added to 50 mL of methanol to obtain a reaction product. The product was heated and refluxed for 24 hours, then cooled to a room temperature, and was put and precipitated in 300 mL of water containing 45 mL of acetic acid. Resulting yellow precipitates were collected via filtration. Then, the precipitates were dissolved in dimethylformamide (DMF) and then re-precipitated in ethyl ether to obtain orange precipitates which in turn were filtered and vacuum-dried. As a result, the compound 1a represented by "1a" in FIG. 1 was obtained.

$^1$H NMR (500 MHz, DMSO) δ8.09-7.95 (m, 2H), 7.66 (dd, J=9.1, 6.3 Hz, 2H), 7.61 (s, 2H), 6.92-6.81 (m, 2H), 6.77-6.68 (m, 2H), 3.00 (s, 6H).

(2) Synthesis of compound 2a

The compound 1a (3.2 g, 11.98 mmol) obtained as described above was dissolved in a mixed solution of 10 mL of DMF and 50 mL of acetonitrile. Then, $K_2CO_3$ (2.2 eq.) was added thereto to produce a mixture. Then, 1,3-dibromopropane (2 eq.) was added in a dropwise manner to the mixture, and then the mixture was heated and refluxed and reacted for about 18 hours. A resulting inorganic salt was filtered to remove the solvent, and then the residue was dissolved again in chloroform and washed three times with saturated NaCl solution. A thus-obtained organic solvent layer was collected, and was dehydrated with $MgSO_4$. Then, the solvent was removed. The residue was purified using a column chromatography (developing solvent condition: DCM (dichloromethane): MeOH (methanol)=95:5). As a result, the compound 2a shown in FIG. 1 as "2a" was obtained.

$^1$H NMR (500 MHz, Acetone) δ8.17-8.10 (m, 2H), 7.74 (d, J=15.4 Hz, 1H), 7.70-7.65 (m, 2H), 7.62 (d, J=15.4 Hz, 1H), 4.26 (t, J=5.9 Hz, 2H), 3.71 (t, J=6.6 Hz, 2H), 2.37 (p, J=6.4 Hz, 2H).

(3) Synthesis of Compound 3a

Tri-tert-butyl 2,2',2"-(1,4,7,10-tetraazacyclododecane-1,4,7-triyl)triacetate (1 eq.) was dissolved in 150 mL of acetonitrile. Then, $K_2CO_3$ (3 eq.) was added thereto to produce a first mixture. Then, the above compound 2a (1.5 eq) was dissolved in a dropwise manner into 10 mL of dimethylformamide to produce a second mixture. Then, the first and second mixtures were mixed in a dropwise manner to produce a mixed solution. Then, the mixed solution was heated and refluxed for 18 hours. A resulting inorganic salt was filtered to remove the solvent and then purified by a column chromatography (developing solvent condition; DCM:MeOH=95:5). As a result, the compound 3a represented by "3a" in FIG. 1 was obtained.

$^1$H NMR (500 MHz, CDCl$_3$) δ8.07-7.93 (m, 2H), 7.78 (d, J=15.4 Hz, 1H), 7.63-7.47 (m, 2H), 7.35 (dd, J=15.4, 2.7 Hz, 1H), 7.01-6.87 (m, 2H), 6.76-6.62 (m, 2H), 4.13 (dt, J=12.7, 5.9 Hz, 2H), 3.73-3.06 (m, 12H), 3.05 (s, 6H), 2.82 (s, J=26.0 Hz, 6H), 2.69-2.23 (m, 7H), 2.04-1.88 (m, 1H), 1.45 (dd, =10.9, 4.1 Hz, 7H).

(4) Synthesis of L$^a$

The compound 3a prepared as described above was dissolved in 10 mL of dichloromethane, and, then, 10 mL of trifluoroacetic acid (excess) was added thereto to produce a mixture. The mixture reacts at a room temperature for 24 hours. After the reaction, the solvent and the remaining trifluoroacetic acid were removed by adding ethanol to the reacted mixture. No separate purification process was performed. Accordingly, the compound L$^a$ represented by "L$^a$" in FIG. 1 was obtained. The obtained compound L$^a$ was confirmed using HR-FAB Mass analysis.

HR-FABMS (m/z): calcd for $C_{34}H_{48}N_5O_8$, 654.3503 ([MH]$^+$); found, 654.3505 ([MH]$^+$).

(5) Synthesis of GdL$^a$

The compound L$^a$ (1 eq.) obtained as described above was dissolved in tertiary distilled water, and gadolinium chloride hexahydrate (1 eq.) was added thereto to produce a mixture. A pH of the mixture was adjusted to 6.5 to 7 using 1N NaOH. The mixture reacts at a room temperature for 48 hours. Thus, orange precipitates were obtained via filtration. Thus, a compound GdL$^a$ was obtained and analyzed using HR-FAB Mass analysis.

HR-FABMS (m/z): calcd for $C_{34}H_{44}GdN_5O_8$, 809.2509 ([MH]$^+$); found, 809.2506 ([MH]$^+$).

Synthesis of Gadolinium Complex (GdL$^b$)

FIG. 2 is a diagram for illustrating a method for synthesizing a gadolinium complex (GdL$^b$) according to an embodiment of the present disclosure. A gadolinium complex (GdL$^b$) according to one embodiment of the present disclosure was synthesized using a synthesis procedure in FIG. 2.

(1) Synthesis of Compound 1b

4'-aminoacetophenone (1 eq.) was dissolved in ethanol and then 50% KOH aqueous solution (potassium hydroxide: 3 eq.) was added thereto to produce a first mixture. Then, p-dimethylaminobenzaldehyde (1.06 eq.) was dissolved in the same amount of ethanol to produce a second mixture. The second mixture was mixed with the first mixture to produce a mixed solution. Then, the mixed solution was heated and refluxed and reacted for 6 hours. A reaction product was precipitated in cold water and then stirred for 24 hours and filtered. Then, orange solid substances obtained by the filtration was purified by a column chromatography (developing solvent condition: DCM (dichloromethane): MeOH (methanol)=95:5). Accordingly, the compound 1b represented by "1b" in FIG. 2 was obtained.

$^1$HNMR (500 MHz, CDCl$_3$) δ7.99-7.85 (m, 2H), 7.76 (d, J=15.4 Hz, 1H), 7.60-7.46 (m, 2H), 7.35 (d, J=15.4 Hz, 1H), 6.69 (d, J=8.4 Hz, 4H), 3.02 (s, 6H).

(2) Synthesis of Compound 2b

The resulting compound 1b (1 eq.) was dissolved in chloroform and then triethylamine (5 eq.) was added thereto to produce a mixture. After an ice bath was set up, chloroacetyl chloride (2 eq.) was added dropwise into the mixture and then the mixture was heated and refluxed and reacted for about 1 hour. When the reaction product was cooled in the ice bath. Then, the product was washed three times with water. A resulting organic solvent layer was collected and dehydrated by adding MgSO$_4$ thereto. Then, the solvent was removed therefrom and thus a red solid substance was obtained, which will be used at a subsequent process without a further separation process. Accordingly, the compound 2b represented by "2b" in FIG. 2 was obtained.

$^1$HNMR (500 MHz, Acetone) δ9.57 (s, 1H), 8.06-7.93 (m, 2H), 7.74-7.67 (m, 2H), 7.61 (d, J=15.4 Hz, 1H), 7.57-7.52 (m, 2H), 7.49 (d, J=15.4 Hz, 1H), 6.69-6.58 (m, 2H), 4.16 (s, 2H), 2.92 (s, 6H).

(3) Synthesis of Compound 3b

Tri-tert-butyl 2,2',2"-(1,4,7,10-tetraazacyclododecane-1,4,7-triyl)triacetate (1 eq.) was dissolved in 150 mL of acetonitrile. Then, $K_2CO_3$ (3 eq.) was added thereto to produce a first mixture. Then, the above compound 2b (1.5 eq) was dissolved in a dropwise manner into 10 mL of dimethylformamide to produce a second mixture. Then, the first and second mixtures were mixed in a dropwise manner to produce a mixed solution. Then, the mixed solution was heated and refluxed for 18 hours. A resulting inorganic salt was filtered to remove the solvent and then purified by a column chromatography (developing solvent condition; DCM:MeOH=95:5). As a result, the compound 3b represented by "3a" in FIG. 2 was obtained.

$^1$H NMR (500 MHz, CDCl$_3$) δ10.86 (s, J=20.0 Hz, 1H), 8.07 (d, J=8.8 Hz, 2H), 7.89 (d, J=8.8 Hz, 2H), 7.75 (d, J=15.4 Hz, 1H), 7.53 (d, J=8.9 Hz, 2H), 7.33 (d, J=15.3 Hz,

1H), 6.75-6.63 (m, 2H), 3.72 (s, J=34.1 Hz, 2H), 3.03 (s, J=4.8 Hz, 6H), 3.01-1.88 (m, 22H), 1.45 (d, J=20.0 Hz, 27H).

(4) Synthesis of $L^b$

The compound 3b prepared as described above was dissolved in 10 mL of dichloromethane, and, then, 10 mL of trifluoroacetic acid (excess) was added thereto to produce a mixture. The mixture reacts at a room temperature for 24 hours. After the reaction, the solvent and the remaining trifluoroacetic acid were removed by adding ethanol to the reacted mixture. No separate purification process was performed. Accordingly, the compound $L^b$ represented by "$L^b$" in FIG. 2 was obtained. The obtained compound $L^b$ was confirmed using HR-FAB Mass analysis.

HR-FABMS (m/z): calcd for $C_{33}H_{44}N_6O_8$, 675.3118 ([MNa]$^+$); found, 675.3114 ([MNa]$^+$).

(5) Synthesis of $GdL^b$

The compound $L^b$ (1 eq.) obtained as described above was dissolved in tertiary distilled water, and gadolinium chloride hexahydrate (1 eq.) was added thereto to produce a mixture. A pH of the mixture was adjusted to 6.5 to 7 using IN NaOH. The mixture reacts at a room temperature for 48 hours. Thus, orange precipitates were obtained via filtration. Then, the purified product was purified by a reverse phase column chromatography (purification condition: water, methanol) Thus, a compound $GdL^b$ was obtained and analyzed using HR-FAB Mass analysis.

HR-FABMS (m/z): calcd for $C_{33}H_{41}GdN_6O_8$, 808.2322 ([MH]$^+$); found, 808.2308 ([MH]$^+$).

Characteristics Evaluation: Relaxibity

The relaxibity for the gadolinium complex $GdL^b$ as obtained above was measured at magnetic field strengths of 1.5 T and 9.4 T respectively as follows.

$T_1$ relaxation time was checked using inversion recovery according to various T1 (inversion times). MRI images were obtained at 35 different T1 values (50 msec to 1750 msec). More specifically, signal intensities at varying 35 inversion times T1 were acquired. Then, the signal intensities are subjected to a minimum non-linear fitting (NLF) to obtain the relaxation time (s). Then, the relaxibity (unit $mM^{-1} s^{-1}$) is obtained using the relaxation time (s) and the concentration (mM) of the contrast agent. The $T_2$ relaxation time is determined as follows. We applied a CPMG (Carr Purcell Meiboon Gill) pulse sequence for various spin-echo measurements. Then, MRI images were obtained from 34 different echo time (TE) values. For TEs, mean values of pixels for various spin-echo measurements were calculated using a nonlinear fitting method. Then, the $T_2$ relaxation time was calculated using the spin-echo measurements. The relaxibity ($mM^{-1}s^{-1}$) was calculated as an inverse of a relaxation time (s) for the contrast agent 1 mM. We calculated $r_1$ using the $T_1$ relaxation time and $r_2$ using the $T_2$ relaxation time.

The relaxibity for Gadovist (trade name, Bayer company) was obtained at 1.5 T and 9.4 T respectively. Results are shown in Table 1 below. In Table 1, a unit of relaxibity is "$mM^{-1}s^{-1}$".

TABLE 1

| Intensity of magnetic field | 1.5 T | | 9.4 T | |
|---|---|---|---|---|
| Relaxibity | $r_1$ | $r_2$ | $r_1$ | $r_2$ |
| compoundGdL$^b$ | 6.24 | 6.79 | 4.60 | 5.71 |
| Gadovist ® | 4.06 | 4.42 | 2.96 | 3.6 |

Referring to Table 1, Gadovist® as a representative contrast agent exhibits a contrast-enhancing effect corresponding to a relaxibity of about 4 $mM^{-1}s^{-1}$ at 1.5 T. However, Gadovist® exhibits a low relaxibity of 2 to 3 $mM^{-1}s^{-1}$ under a significantly high magnetic field of 9.4 T.

However, the compound $GdL^b$ according to one embodiment of the present disclosure not only exhibits a very high contrast-enhancing effect corresponding to a level of 6 to 7 $mM^{-1} s^{-1}$ at 1.5 T but also not only exhibits a higher value of the relaxibity than that of the Gadovist® in the high magnetic field of 9.4 T. In particular, it may be confirmed that $r_1$ as a relaxibity corresponding to an effect of brightening a video signal has a high value of 4 $mM^{-1} s^{-1}$ or greater. That is, the compound $GdL^b$ according to one embodiment of the present disclosure does not deteriorate the contrast-enhancing effect even in a high magnetic field and exhibits excellent contrasting characteristics. Although not shown in Table 1, it may be confirmed that in $GdL^a$ according to one embodiment of the present disclosure, the high relaxivity is exhibited in a high magnetic field with substantially the same tendency as that in the compound $GdL^b$ according to one embodiment.

In addition to Gadovist, the relaxibities at 1.5 T of macrocylic type commercialized contrast agents such as Magnevist (product name), Dotarem (product name), Omniscan (trade name), ProHance (trade name) were in a range of 3 to 4 $mM^{-1}s^{-1}$. Generally, when considering that as the magnetic field strength increases, the relaxibity decreases, the relaxibities of the above macrocylic type commercialized contrast agents will also decrease to the Gadovist's level below 3 $mM^{-1}s^{-1}$ at the high magnetic field of 7 T or greater. Although there are linear type contrast agents that exhibit the high relaxibity in high magnetic fields, these linear type contrast agents cause a partial dissociation of coordinated metal ions, that is, gadolinium ions, and thus the use of the contrast agents is very dangerous to the human body, which may not be the case for the macrocylic type contrast agents. Adverse effects such as induction of nephrogenic systemic fibrosis in the renal patient or long-term accumulation of the gadolinium on the brain due to the dissociation of the gadolinium ions in the linear type contrast agent has been reported. When considering that the contrast agents are injected directly into animals or humans, it is essential that biocompatibility and stability thereof should be high. Thus, although the linear type contrast agent is superior in terms of contrast-enhancing effect because it has the high relaxibity, the linear type contrast agent is not suitable in terms of biostability.

To the contrary, the gadolinium complex according to the present disclosure is based on the macrocylic type and has a high stability and improved relaxibity in a high magnetic field. Thus, the gadolinium complex according to the present disclosure may be widely used as an optimized gadolinium-based contrast agent with improved biostability and contrast-enhancing effect.

Characteristics Evaluation: In Vitro Binding Affinity to Beta Amyloid Oligomer beta amyloid (Aβ) may be present in a form of a monomer, an oligomer or a fibril. Among them, the beta amyloid oligomer is attracting attention as a substance causing neurotoxicity. Therefore, a following experiment was carried out to check the binding affinity thereof to the beta amyloid oligomer.

Beta amyloid protein was incubated to prepare a beta amyloid oligomer. For comparison, each of the conventional Gadovist® and the compound $GdL^b$ according to one embodiment of the present disclosure was treated with the beta amyloid oligomer. After 24 hours, a residual contrast agent was washed, and $T_1$-weighted images were obtained to compare binding affinities of the two contrast agents to the beta amyloid oligomers. The results are shown in FIG. 3.

FIG. 3 is a graph showing the in vitro binding affinity evaluation results of the gadolinium complex ($GdL^b$) according to one embodiment of the present disclosure to the beta amyloid oligomer.

Referring to FIG. 3, as for PBS (phosphate buffer saline), Gadovist® and $GdL^b$, the gadolinium complex ($GdL^b$) according to one embodiment of the present disclosure has a higher signal enhancement effect responding to the beta amyloid oligomer than the extracelluar fluid (ECF) Gadovist®. This may be due to a fact that the gadolinium complex (GdLb) according to the present disclosure targets and binds to the beta amyloid oligomer and thus the relaxibity is increased due to a change of a rotation correlation coefficient (τR) compared to the Gadovist®.

Characteristics Evaluation: Comparison Between In Vivo MR Imaging for Dementia Disease Model and Ex Vivo Fluorescence Image for Dementia Disease Model For checking the affinity of the gadolinium complex ($GdL^b$) to the 5XFAD dementia disease model, the gadolinium complex ($GdL^b$) according to one embodiment of the present disclosure was directly injected into the cerebral ventricles. Then, the contrast-enhancing effect in the brain tissue was confirmed. The contrast enhancement was observed in a local area of the cerebral cortex. After the experiment, the brain was extracted and cryo-embedding was performed thereto to obtain a brain slice. The beta amyloid plaque of the brain slice was stained with thioflavin S and the beta amyloid plaque was identified via fluorescence microscopy. The results are shown in FIG. 4.

FIG. 4 shows comparison between in vivo MR imaging analysis using the gadolinium complex ($GdL^b$) and ex vivo fluorescence image for a dementia disease model according to one embodiment of the present disclosure.

Referring to FIG. 4, (a) represents the MR image, (b) shows a fluorescence image, (c) shows a photograph in which (a) and (b) images are superposed with each other. Referring to these images and photograph, it may be confirmed from the photograph (c) that the contrast-enhanced localized region in the MR image ($T_1$-weighted image) occurring after the injection of the gadolinium complex ($GdL^b$) according to one embodiment of the present disclosure as shown in (a) substantially coincides with the position of the beta amyloid plaque in the fluorescence image as shown in (b).

In FIG. 4, (d) is a fluorescence image when a gadolinium complex ($GdL^b$) according to an embodiment of the present disclosure is used, (e) is a fluorescence image when using thiopurine S, and (f) is a photograph in which (d) and (e) are superimposed with each other. Referring to these images and photograph, it may be confirmed that the gadolinium complex ($GdL^b$) also fluoresces so that a fluorescent image can be obtained as shown in (d). Further, it may be confirmed from the photograph (f) that the position of the beta amyloid plaque to which the gadolinium complex ($GdL^b$) targets and binds substantially coincides with a position of the beta amyloid plaque to which the thiopurine S targets and binds.

That is, it may be confirmed from the results that the gadolinium complex ($GdL^b$) according to one embodiment of the present disclosure has binding affinity to both beta amyloid oligomer and 5XFAD dementia model and may reliably target the beta amyloid. Thus, the gadolinium complex according to the present disclosure may be suitably used as a MRI contrast agent targeting the beta amyloid oligomer.

Although the present disclosure has been described with reference to preferred embodiments of the present disclosure, it will be understood by those skilled in the art that various changes in form and details may be made thereto without departing from the spirit and scope of the present disclosure as set forth in the following claims.

What is claimed is:

1. A gadolinium complex expressed as a following Chemical Formula 1:

[Chemical Formula 1]

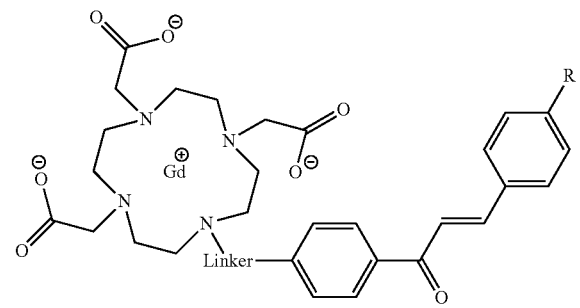

wherein the linker represents *—$(CH_2)_n$-A-*,
wherein n indicates an integer of 0 to 5,
wherein A represents *—COO—*, *—CO—*, *—CONH—*, *—O—* or *—$C_5N(R_aR_b)$—*,
wherein R represents a hydrogen atom, a hydroxyl group, an alkyl group having 1 to 5 carbon atoms, an alkoxy group having 1 to 5 carbon atoms, an aryl group having 5 to 20 carbon atoms, a heteroaryl group having 4 to 20 carbon atoms or *—$NR_1R_2$,
wherein each of $R_a$, $R_b$, $R_1$ and $R_2$ independently represents a hydrogen atom or an alkyl group having 1 to 5 carbon atoms.

2. The gadolinium complex of claim 1, wherein the gadolinium complex represented by the Chemical Formula 1 includes a compound represented by a following Chemical Formula 2:

[Chemical Formula 2]

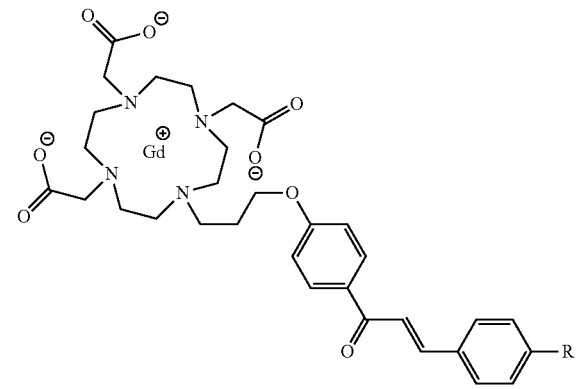

wherein R represents a hydrogen atom, a hydroxyl group, an alkyl group having 1 to 5 carbon atoms, an alkoxy group having 1 to 5 carbon atoms, an aryl group having 5 to 20 carbon atoms, a heteroaryl group having 4 to 20 carbon atoms or *—NR$_1$R$_2$, wherein each of R$_1$ and R$_2$ independently represents a hydrogen atom or an alkyl group having 1 to 5 carbon atoms.

3. The gadolinium complex of claim 2, wherein in the Chemical Formula 2, R represents a dimethylamine group.

4. The gadolinium complex of claim 1, wherein the gadolinium complex represented by the Chemical Formula 1 includes a compound represented by a following Chemical Formula 3:

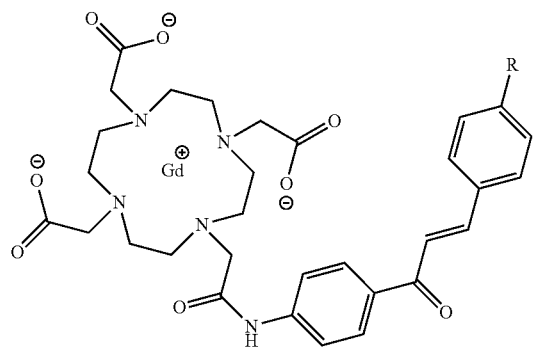

[Chemical Formula 3]

wherein R represents a hydrogen atom, a hydroxyl group, an alkyl group having 1 to 5 carbon atoms, an alkoxy group having 1 to 5 carbon atoms, an aryl group having 5 to 20 carbon atoms, a heteroaryl group having 4 to 20 carbon atoms or *—NR$_1$R$_2$, wherein each of R$_1$ and R$_2$ independently represents a hydrogen atom or an alkyl group having 1 to 5 carbon atoms.

5. The gadolinium complex of claim 4, wherein in the Chemical Formula 3, R represents a dimethylamine group.

6. The gadolinium complex of claim 1, wherein gadolinium in the gadolinium complex is coordinated with at least one water molecule.

7. The gadolinium complex of claim 4, wherein the gadolinium complex exhibits a relaxivity of greater than or equal to 4 mM$^{-1}$s$^{-1}$ in a high magnetic field range of 7 T or greater.

8. The gadolinium complex of claim 1, wherein the gadolinium complex has a relaxibity (r$_1$) dependent on a T$_1$ relaxation time obtained based on an inversion time and a relaxibity (r$_2$) dependent on a T$_2$ relaxation time obtained based on an echo time, wherein each of the relaxibity (r$_1$) and relaxibity (r$_2$) is greater than or equal to 4 mM$^{-1}$s$^{-1}$ in a high magnetic field range of 7 T or greater.

9. The gadolinium complex of claim 1, wherein the gadolinium complex exhibits a relaxivity of 4 mM$^{-1}$s$^{-1}$ to 7 mM$^{-1}$ s$^{-1}$ in a high magnetic field range of 7 T to 10 T.

10. A MRI (magnetic resonance image) contrast agent containing a gadolinium complex expressed as a following Chemical Formula 1:

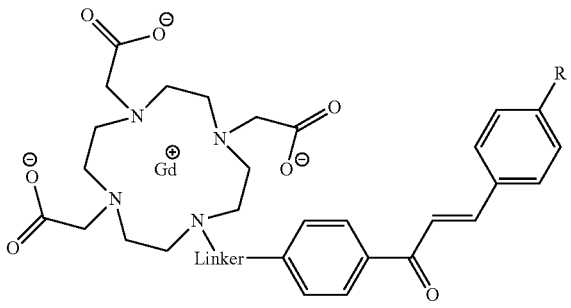

[Chemical Formula 1]

wherein the linker represents *—(CH$_2$)$_n$-A-*, wherein n indicates an integer of 0 to 5, wherein A represents *—COO—*, *—CO—*, *—CONH—*, *—O—* or *—C$_5$N(R$_a$R$_b$)—*, wherein R represents a hydrogen atom, a hydroxyl group, an alkyl group having 1 to 5 carbon atoms, an alkoxy group having 1 to 5 carbon atoms, an aryl group having 5 to 20 carbon atoms, a heteroaryl group having 4 to 20 carbon atoms or *—NR$_1$R$_2$, wherein each of R$_a$, R$_b$, R$_1$ and R$_2$ independently represents a hydrogen atom or an alkyl group having 1 to 5 carbon atoms.

11. The contrast agent of claim 10, wherein the contrast agent exhibits a relaxivity of 4 mM$^{-1}$s$^{-1}$ to 7 mM$^{-1}$ s$^{-1}$ in a high magnetic field range of 7 T to 10 T.

12. The contrast agent of claim 10, wherein the contrast agent has a relaxibity (r$_1$) dependent on a T$_1$ relaxation time obtained based on an inversion time and a relaxibity (r$_2$) dependent on a T$_2$ relaxation time obtained based on an echo time, wherein each of the relaxibity (r$_1$) and relaxibity (r$_2$) is greater than or equal to 4 mM$^{-1}$s$^{-1}$ in a high magnetic field range of 7 T or greater.

13. The contrast agent of claim 10, wherein the gadolinium complex represented by the Chemical Formula 1 may include at least one water molecule coordinated with gadolinium.

14. The contrast agent of claim 10, wherein the MRI contrast agent targets beta amyloid.

15. A method for producing a gadolinium complex, the method including:

synthesizing a chalcone-based compound represented by a following Chemical Formula 1-1;

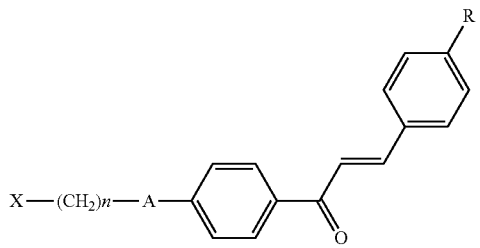

[Chemical Formula 1-1]

synthesizing a compound represented by a following Chemical Formula 1-2 using the compound represented by the Chemical Formula 1-1;

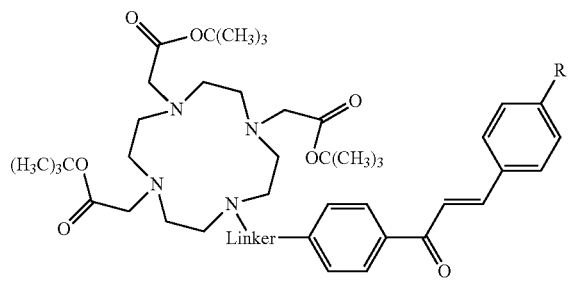

[Chemical Formula 1-2]

producing a ligand represented by a following Chemical Formula 1-3 using the compound represented by the Chemical Formula 1-2; and

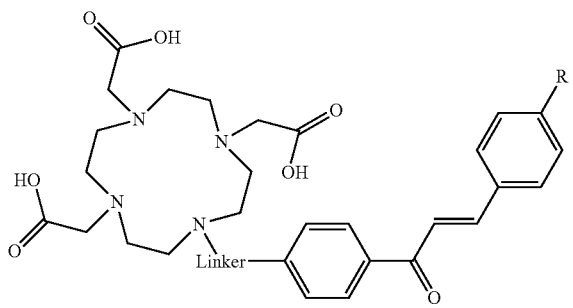

[Chemical Formula 1-3]

synthesizing a gadolinium complex represented by a following Chemical Formula 1 using the ligand represented by the Chemical Formula 1-3 and gadolinium chloride hexahydrate:

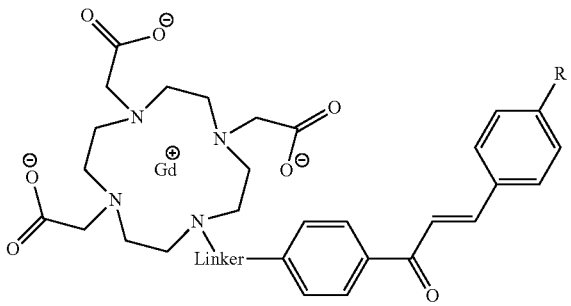

[Chemical Formula 1]

wherein in the Chemical Formula 1-1, X represents a halogen atom, wherein the linker in each of the Chemical Formulas 1-2 and 1-3 and Chemical Formula 1 represents *—$(CH_2)_n$-A-*, wherein in the Chemical Formula 1-1 and in the linker of each of the Chemical Formulas 1-2, and 1-3 and Chemical Formula 1, n represents an integer of 0 to 5, wherein A represents *—COO—*, *—CO—*, *—CONH—*, *—O—* or *—$C_5N(R_aR_b)$—*, wherein R represents a hydrogen atom, a hydroxyl group, an alkyl group having 1 to 5 carbon atoms, an alkoxy group having 1 to 5 carbon atoms, an aryl group having 5 to 20 carbon atoms, a heteroaryl group having 4 to 20 carbon atoms or *—$NR_1R_2$, wherein each of $R_a$, $R_b$, $R_1$ and $R_2$ independently represents a hydrogen atom or an alkyl group having 1 to 5 carbon atoms.

16. The method of claim 15, wherein synthesizing the chalcone-based compound includes:

mixing and reacting p-hydroxyacetophenone, a KOH aqueous solution and p-dimethylaminobenzaldehyde with methanol to obtain a precipitate; and reacting the precipitate with 1,3-dibromopropane to produce a compound having the Chemical Formula 1-1 in which R is a dimethylamine group, n is 3, A is *—O—*, and X is Br.

17. The method of claim 15, wherein synthesizing the chalcone-based compound includes:

mixing and reacting 4'-aminoacetophenone, KOH aqueous solution, p-dimethylaminobenzaldehyde with ethanol to obtain a precipitate; and reacting the precipitate with chloroacetyl chloride to produce a compound having the Chemical Formula 1-1 in which R is a dimethylamine group, n is 1, A is *—CONH—*, and X is Cl.

* * * * *